United States Patent

Alvain

(10) Patent No.: US 8,858,531 B2
(45) Date of Patent: Oct. 14, 2014

(54) CONNECTION ASSEMBLY FOR A DRUG DELIVERY DEVICE, AND METHOD FOR MAKING THIS ASSEMBLY

(75) Inventor: Olivier Alvain, Seyssins (FR)

(73) Assignee: Becton Dickinson France, Le Pont-de-Claix (FR)

( * ) Notice: Subject to any disclaimer, the term of this patent is extended or adjusted under 35 U.S.C. 154(b) by 282 days.

(21) Appl. No.: 13/379,254

(22) PCT Filed: Jun. 24, 2009

(86) PCT No.: PCT/IB2009/006555
§ 371 (c)(1),
(2), (4) Date: Feb. 9, 2012

(87) PCT Pub. No.: WO2010/150041
PCT Pub. Date: Dec. 29, 2010

(65) Prior Publication Data
US 2012/0130351 A1    May 24, 2012

(51) Int. Cl.
*A61M 39/10* (2006.01)
*A61M 5/34* (2006.01)
*A61M 5/31* (2006.01)

(52) U.S. Cl.
CPC ............... *A61M 5/347* (2013.01); *A61M 5/344* (2013.01); *A61M 5/3134* (2013.01)
USPC .......................................... 604/533; 604/535

(58) Field of Classification Search
CPC ............................. A61M 39/10; B29C 65/02
USPC .................................................. 604/533, 535
See application file for complete search history.

(56) References Cited

U.S. PATENT DOCUMENTS

| 1,967,513 | A |   | 7/1934  | Ponte |
| 3,402,714 | A |   | 9/1968  | Higgins et al. |
| 3,889,351 | A | * | 6/1975  | Tischlinger ..................... 29/447 |
| 4,676,530 | A |   | 6/1987  | Nordgren et al. |
| 4,927,417 | A |   | 5/1990  | Moncada et al. |
| 5,215,538 | A | * | 6/1993  | Larkin .......................... 604/249 |
| 6,652,509 | B1 | * | 11/2003 | Helgren et al. ............... 604/535 |
| 2002/0069616 | A1 |   | 6/2002 | Odell et al. |

(Continued)

FOREIGN PATENT DOCUMENTS

| FR | 387123     | 2/1908  |
| GB | 1215361    | 12/1970 |
| JP | 200324441 A | 1/2003 |

*Primary Examiner* — Nicholas Lucchesi
*Assistant Examiner* — Gerald Landry, II
(74) *Attorney, Agent, or Firm* — The Webb Law Firm

(57) ABSTRACT

This connection assembly includes a tip defining a longitudinal axis and including a mounting area for mounting an adaptor thereon, and the adaptor including a mounting portion of thermoplastic material, forming a radial surface, which define a mounting opening for mounting the adaptor onto the tip.

The mounting area includes at least one first portion having an outer surface which is located at a first distance from the longitudinal axis (A) and at least one second portion, adjacent to the first portion, having an outer surface which is located at a second distance from the longitudinal axis, the second distance being different from the first distance, the radial surface being located after assembly of the adaptor over the first portion and the second portion;

The mounting opening and the at least one first portion and second portion are so dimensioned such that the radial surface of the mounting portion is in close contact with the outer surfaces of both the first portion and the second portion.

11 Claims, 4 Drawing Sheets

(56) References Cited

U.S. PATENT DOCUMENTS

| | | | |
|---|---|---|---|
| 2003/0023207 A1* | 1/2003 | Donnan et al. | 604/181 |
| 2003/0036735 A1* | 2/2003 | Jepson et al. | 604/247 |
| 2004/0077298 A1* | 4/2004 | Sjolander | 451/342 |
| 2005/0124970 A1* | 6/2005 | Kunin et al. | 604/508 |
| 2005/0197646 A1* | 9/2005 | Connell et al. | 604/533 |
| 2006/0178627 A1* | 8/2006 | Geiger et al. | 604/111 |
| 2007/0106264 A1* | 5/2007 | Proulx et al. | 604/533 |
| 2008/0172039 A1* | 7/2008 | Raines | 604/533 |
| 2010/0007134 A1* | 1/2010 | Elton et al. | 285/31 |
| 2010/0063481 A1* | 3/2010 | Hoffman et al. | 604/537 |
| 2011/0071504 A1* | 3/2011 | Saltell et al. | 604/533 |
| 2011/0125085 A1* | 5/2011 | McGill et al. | 604/29 |
| 2011/0209785 A1* | 9/2011 | Elton et al. | 137/561 R |

\* cited by examiner

CONNECTION ASSEMBLY FOR A DRUG DELIVERY DEVICE, AND METHOD FOR MAKING THIS ASSEMBLY

The present invention relates to a connection assembly for a drug delivery device, including a tip and an adaptor. This tip can be in particular the tip of a syringe body, for example made of glass, allowing the connection of an injection needle to this syringe body. Said adaptor can be in particular a Luer type connector.

The invention also relates to a method for making said connection assembly.

It is known to make safe the connection of a syringe needle to the tip which a syringe body includes, by means of an adaptor mounted on the tip, this adaptor being internally threaded in order to receive, by screwing, a threaded end included in the end of the needle which is intended to be connected to the syringe body. It is known in the same manner to make safe the connection of a medical duct to a tip of the Luer type by means of adaptor in the form of a Luer type connector.

On a purely illustrative basis, FIGS. 1 to 3 represent such a known adaptor 1 and the tip 2 of a syringe body intended for the connection of a needle by the means of this adaptor 1. The adaptor 1 includes a peripheral wall 3 comprising an internal thread 4 and, at a proximal end, a plurality of radial legs 5, six radial legs 5 for example, which free ends define an opening 6 for the assembly of the adaptor 1 on the tip 2. The tip 2 includes a tapered distal portion 7 and a cylindrical proximal portion 8, separated by a shoulder 9. The adaptor 1 is engaged on the tapered distal portion 7 until the radial legs 5 snap beyond the shoulder 9.

It is to be understood that "proximal" and "distal" are considered with respect to the direction of the injection.

The adaptor 1 is supposed to be immobile with respect to the tip 2 thanks to essentially friction forces present between the radial legs 5 and this portion 8 and partly thanks to the shoulder 9. However this immobilization is not always perfectly assured, making the connection of a needle or of a duct more difficult, and especially not ensuring maintaining this connection during use, with the serious consequences which can result concerning medical equipment and in particular injection equipment.

Moreover, said immobilization tends to be modified when the connection assembly made of adaptor 1 and tip 2 assembly is warmed in an autoclave for sterilization.

The present invention aims to overcome these disadvantages.

The connection assembly which it relates to includes, in a known way, a tip and an adaptor, said tip having a longitudinal axis and including a mounting area for mounting said adaptor thereon, and said adaptor including a mounting portion of thermoplastic material, forming a radial surface which defines a mounting opening for mounting said adaptor onto said tip.

According to the invention, said mounting area includes at least one first portion having an outer surface which is located at a first distance from said longitudinal axis and at least one second portion, adjacent to said first portion, having an outer surface which is located at a second distance from said longitudinal axis, said second distance being different from said first distance, said radial legs being located after assembly over said first portion and said second portion;

said mounting opening and said at least one first portion and second portion are so dimensioned one with respect to the other that said radial surface of said mounting portion is in close contact with the outer surfaces of both said first portion and said second portion.

The process includes, in a known way, the step consisting in engaging said adaptor on said mounting area.

According to the invention, the process further includes the steps consisting in:

arranging in said mounting area at least one first portion having an outer surface which is located at a first distance from said longitudinal axis and at least one second portion, adjacent to said first portion, having an outer surface which is located at a second distance from said longitudinal axis, said second distance being different from said first distance, said radial legs or wall being located after assembly over said first portion and said second portion;

providing said mounting portion of said adaptor and said at least one first portion and second portion so that said mounting portion is compressed in directions perpendicular to said longitudinal axis when said mounting portion is engaged over said first portion and said second portion;

engaging said mounting portion over said first portion and said second portion;

in this engagement position, exposing the connection assembly to a temperature sufficient to allow the thermoplastic material of said mounting portion to creep;

maintaining this temperature for a sufficient duration to allow the creeping of the thermoplastic material of said mounting portion around or into said first portion and said second portion, so that said radial surface of said mounting portion is in close contact with the outer surfaces of both said first portion and said second portion;

allowing said connection assembly to cool to a temperature in which said thermoplastic material has returned to a non plastic state.

Thus, according to the invention, the mounting opening and the mounting area are so designed to generate, in the mounting position, a radial constraint in said mounting portion positioned over said first and second portions, and the thermoplastic material of this mounting portion is warmed so as to allow the radial constraint undergone by this mounting portion to release in the form of a creeping of the material constituting this mounting portion around said first and second portions.

The invention thus implements a mechanical assembly by complementary shapes, ensuring a perfect axial immobilization of the adaptor with respect to the tip and making it possible to obtain, due to the increased surface of contact between said mounting portion and said first and second portions, a higher degree of immobilization in rotation of the adaptor. The resistance of the connection between the adaptor and the tip, obtained in accordance with the invention, can be considered as being about three times higher than that of the connection obtained in accordance with the technique according to the prior art. This increased resistance facilitates the connection but also, and especially, is sufficient to ensure a perfect connection in all the situations that can be met in a current use.

It appears moreover that the immobilization obtained in accordance with the invention remains sufficient after one or several sterilizations of the connection assembly.

Preferably, said mounting portion and at least one of said first portion and said second portion are so dimensioned one with respect to the other that said mounting portion is compressed in a direction perpendicular to said longitudinal axis when this mounting portion is located over said first portion and said second portion.

This residual radial compression contributes to ensure the perfect axial immobilization and the immobilization in rotation of the adaptor with respect to the tip.

Preferably, said first portion is in the form of a circumferential rib or groove centred on said longitudinal axis and said second portion is in the form of a circumferential surface centred on said longitudinal axis, adjacent said rib or groove, said first distance and second distance being the respective radiuses of said rib or groove and circumferential surface.

In an embodiment, at least one of said outer surface of said first portion and of said second portion exhibit, a round cross-section in a plane containing said longitudinal axis.

At least one of said outer surface of said first portion and of said second portion can also contain at least one ridge when seen in cross-section in a plane containing said longitudinal axis.

At least one of said outer surface of said first portion and of said second portion can also contain a surface parallel to said longitudinal axis when seen in cross-section in a plane containing said longitudinal axis.

At least one of said outer surface of said first portion and of said second portion can also contain a surface non parallel to said longitudinal axis, when seen in cross-section in a plane containing said longitudinal axis, said first distance and said second distance being then the minimum distance of this first or second portion to said longitudinal axis.

At least one of said outer surface of said first portion or of said second portion exhibit a cylindrical surface; at least one of said outer surface of said first portion or of said second portion can also exhibit a tapered surface.

The difference between said second distance and said first distance is preferably in the range of 0.05 mm to 0.20 mm.

Concerning the method, in said step of providing said mounting portion and at least one of said first portion and said second portion, this step can be such that said mounting portion is still compressed when said connection assembly is allowed to cool.

Said thermoplastic material can be a polycarbonate, said temperature being then between 40° C. and 150° C. and said sufficient duration being between 30 minutes and 24 hours.

The invention will be readily understood, and other characteristics and advantages of this one will appear, in reference to the annexed diagrammatic drawing, representing, as non restrictive examples, several possible embodiments of the connection assembly which it relates to.

Figure 1:
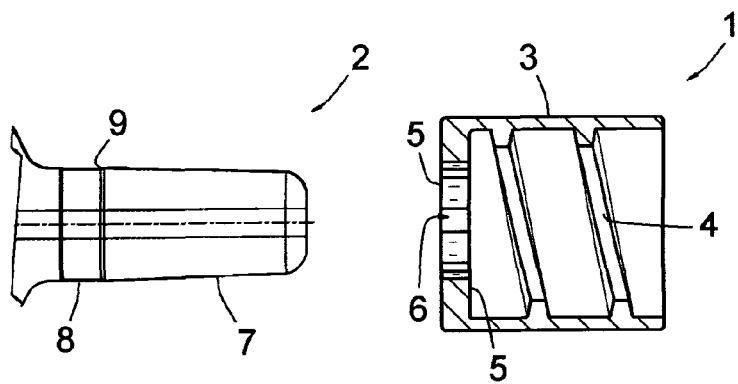
FIG. 1 is a side view, partially in cross section, of a connection assembly according to the prior art, including a tip and a adaptor, before mounting.
Figure 2:
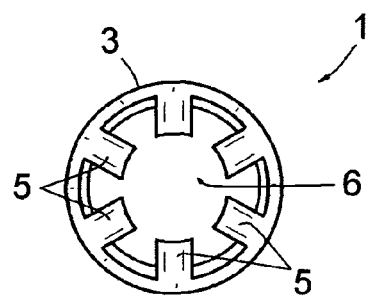
FIG. 2 is a proximal end view of the adaptor.
Figure 3:
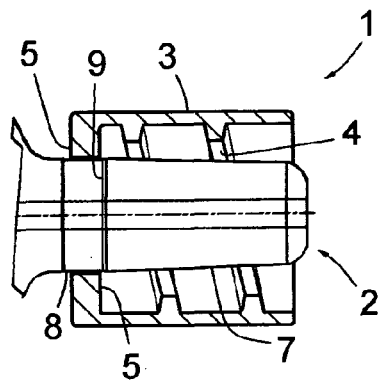
FIG. 3 is a view similar to FIG. 1, after mounting the adaptor on the tip.
Figure 4:
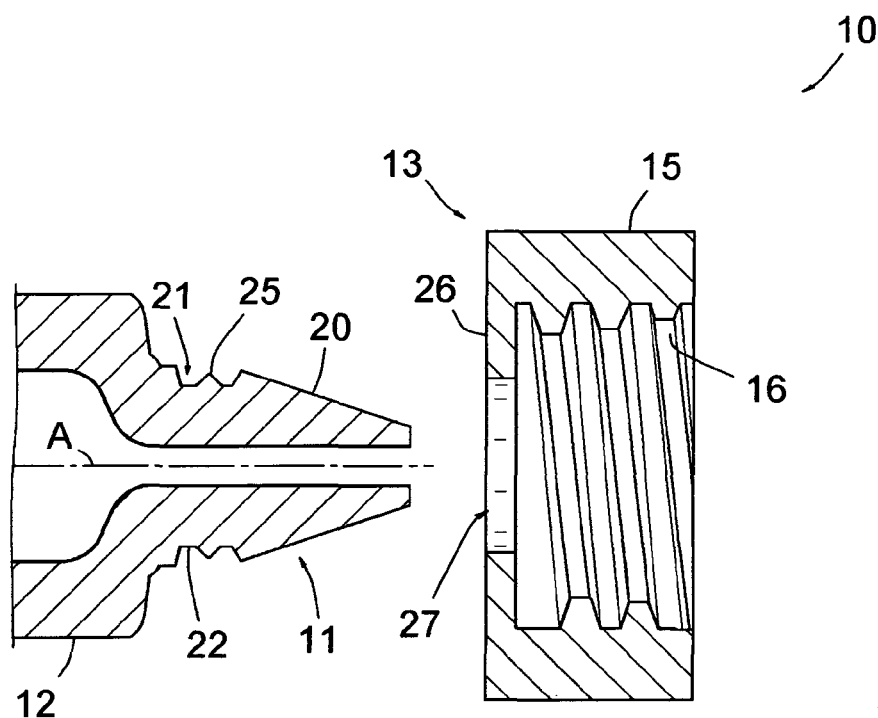
FIG. 4 is a side view in cross section of a first embodiment of a connection assembly according to the invention, before mounting a adaptor on a tip which this connection assembly includes.

For simplification, the parts or elements of one embodiment which are found identically or similarly in the other embodiment will be identified using the same numerical references and will not be described again.

FIGS. 4-7 show a connection assembly 10 for connecting an injection needle or a medical connector (not shown) to the tip 11 of a syringe body 12, for example made of glass. The connection assembly 10 includes said tip 11 and a adaptor 13 which is a Luer type connector, i.e. comprising a peripheral wall 15 and an internal thread 16. The needle or connector has an enlarged proximal end part provided with a thread allowing it to be threaded in the adaptor 13.

The tip 11 has a tapered distal portion 20 and a proximal mounting area 21 with the substantial form of a groove, for mounting the adaptor 13 thereon.

In the embodiment of FIGS. 4-7, the tip 11 is a revolution part having a revolution longitudinal axis A.

The mounting area 21 is delimited by a cylindrical bottom 22 and proximal and distal shoulders. It comprises an annular projection 25 centred on the axis A, projecting from said bottom 22. This projection 25 has a triangular cross section as seen in FIGS. 4-7, thus has an outer ridge located at a distance from said longitudinal axis A which is greater than the distance at which said bottom 22 is located with respect to said longitudinal axis A.

Figure 5:
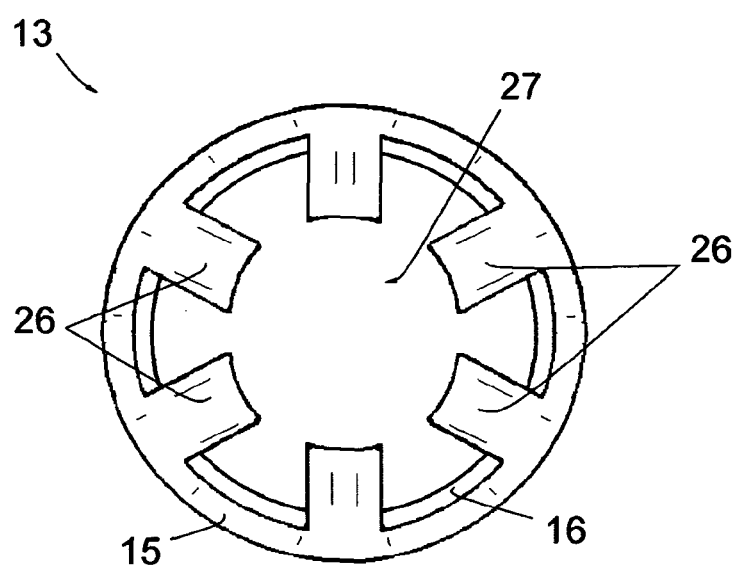
FIG. 5 is a proximal end view of the adaptor.

The adaptor 13 is made of thermoplastic material, particularly of a polycarbonate. At its proximal end, it has at least one radial leg 26, for example six radial legs, regularly arranged on the circumference of the adaptor 13, as shown in FIG. 5. These radial legs 26 form a mounting portion for mounting said adaptor 13 onto said tip 11, the free ends of the radial legs 26 defining a radial surface which forms a mounting opening 27. This opening 27 has a smaller diameter than the diameter of the outer ridge of the projection 25, the difference between these diameter being in the range of 0.05 mm to 0.20 mm.

Figure 6:
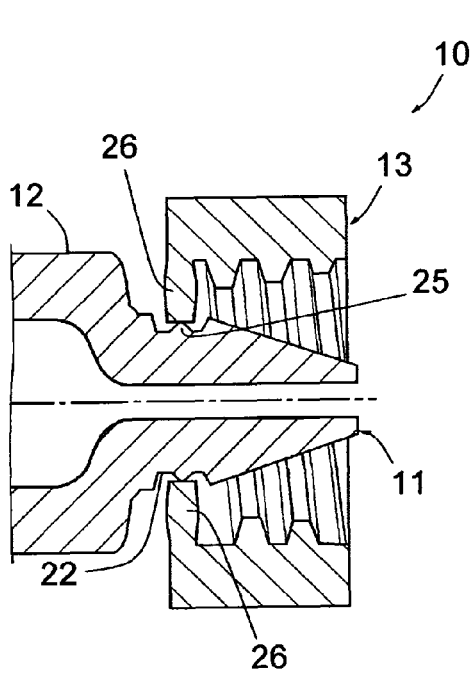
FIG. 6 is a view similar to FIG. 4 in a subsequent step of the mounting process for mounting the adaptor on the tip.

The legs 26 are thus compressed in a direction perpendicular to said longitudinal axis A when these legs are engaged on said outer ridge of said projection 25, as shown on FIG. 6.

The radial legs 26 could be replaced, in an other embodiment, by a continuous radial wall.

Figure 7:
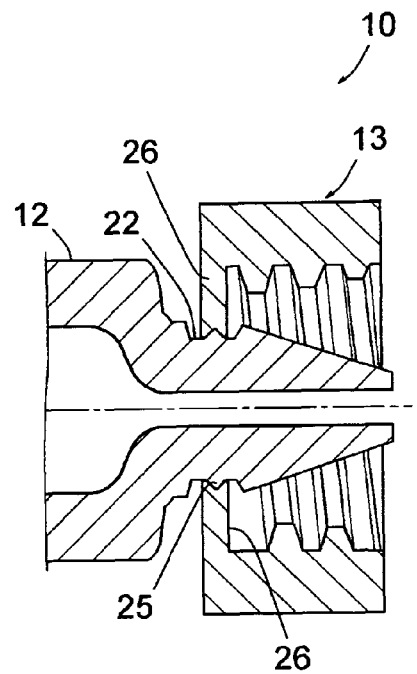
FIG. 7 is a view similar to FIG. 6, the adaptor being mounted on the tip.

The method for mounting said adaptor 13 on said mounting area 21 of said tip 11 includes the following steps:

engaging said adaptor 13 on said tapered distal portion 20 and then on said mounting area 21, until said free ends of the legs 26 are engaged on said projection 25 and over the bottom 22 of the area 21, and are thus radially compressed as shown on FIG. 6;

in this engagement position, exposing the connection assembly 10 to a temperature between 40° C. and 150° C. during 30 minutes and 24 hours, so as to allow the thermoplastic material of said radial legs 26 or wall to creep on the projection 25, on each side of the ridge thereof, until it reaches said bottom 22 of the mounting area 21, thus encompassing the projection 25; the free ends of said radial legs 26 snugly fit with said projection 25 and bottom 22, i.e. are in close contact with both said projection 25 and bottom 22, as shown in FIG. 7;

allowing said connection assembly 10 to cool to a temperature in which said thermoplastic material hardens again.

The connection assembly thus implements a mechanical assembly by complementary shapes, ensuring a perfect axial immobilization of the adaptor 13 with respect to the tip 11, making it possible to obtain, due to the increased surface of contact between said radial legs 26 and said projection 25 and bottom 22, a higher degree of immobilization in rotation of the adaptor 13. The resistance of the connection between the adaptor 13 and the tip 11 is about three times higher than that of the connection obtained in accordance with the technique according to the prior art. This increased resistance facilitates the connection but also, and especially, is sufficient to ensure a perfect connection in all the situations that can be met in a current use.

Figure 8:
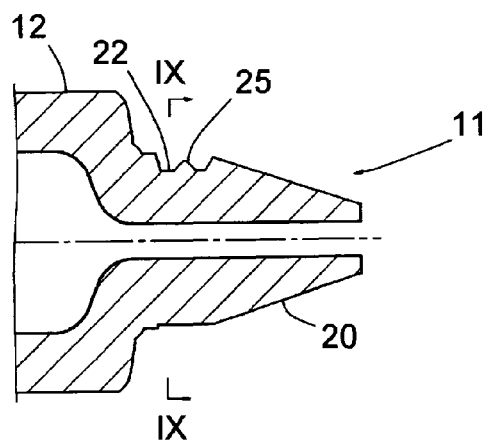
FIG. 8 is a view similar to FIG. 4 of a tip according to another embodiment.
Figure 9:
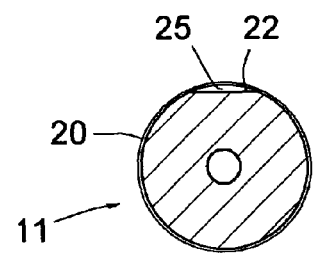
FIG. 9 is a cross section of the tip of FIG. 8 along the line IX-IX of FIG. 8.

FIGS. 8 and 9 show an embodiment in which the mounting area 21 and the projection 25 are not annular but extend only over a part of the circumference of the tip 11. In this case, not all of the radial legs 26 cooperate with the projection 25 and bottom 22 but only a reduced number of them, one, two or three of them, according to the angular position of the adaptor 13 with respect to the tip 11, in the embodiment shown.

Figure 10:
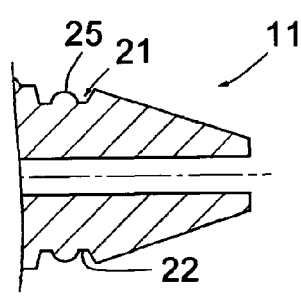
FIG. 10 is a view similar to FIG. 8 of a tip according to another embodiment.

FIG. 10 shows an embodiment in which the projection 25 is a circumferential rounded rib. The material of the legs 26 creeps around the rib 31 until it reaches the bottom 22 of the area 21, in a similar way than described above.

Figure 11:
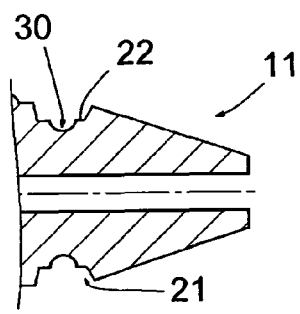
FIG. 11 is a view similar to FIG. 8 of a tip according to another embodiment.

FIG. 11 shows an embodiment in which the projection 25 is replaced by a circumferential rounded groove 30. The legs 26 bear against said bottom 22 of the mounting area 21 in said engagement position and, when their material is warmed, creeps into said groove 30.

Figure 12:
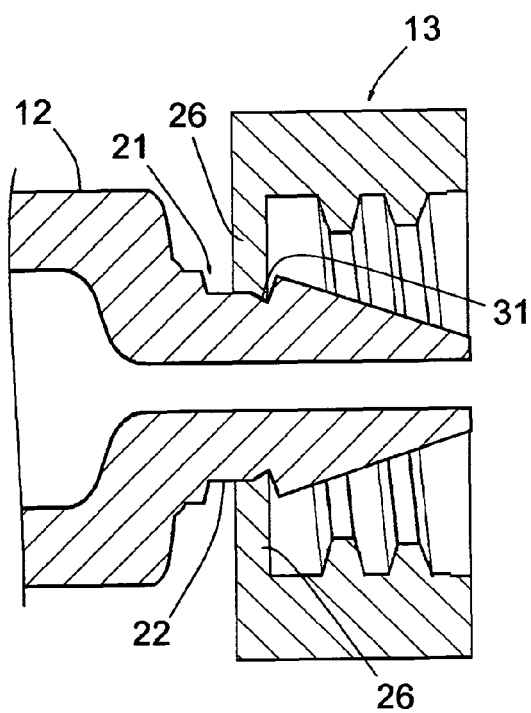
FIG. 12 is a view similar to FIG. 7 of a tip according to another embodiment.

FIG. 12 shows an embodiment in which the mounting area 21 includes a circumferential groove 31, formed by a hollow portion located adjacent the distal shoulder between the mounting area 21 and the tapered distal part 20 of the tip 11. In the same way than for the embodiment of FIG. 11, the legs 26 bear against said bottom 22 in said engagement position and, when their material is warmed, they creep into said groove 31.

Figure 13:
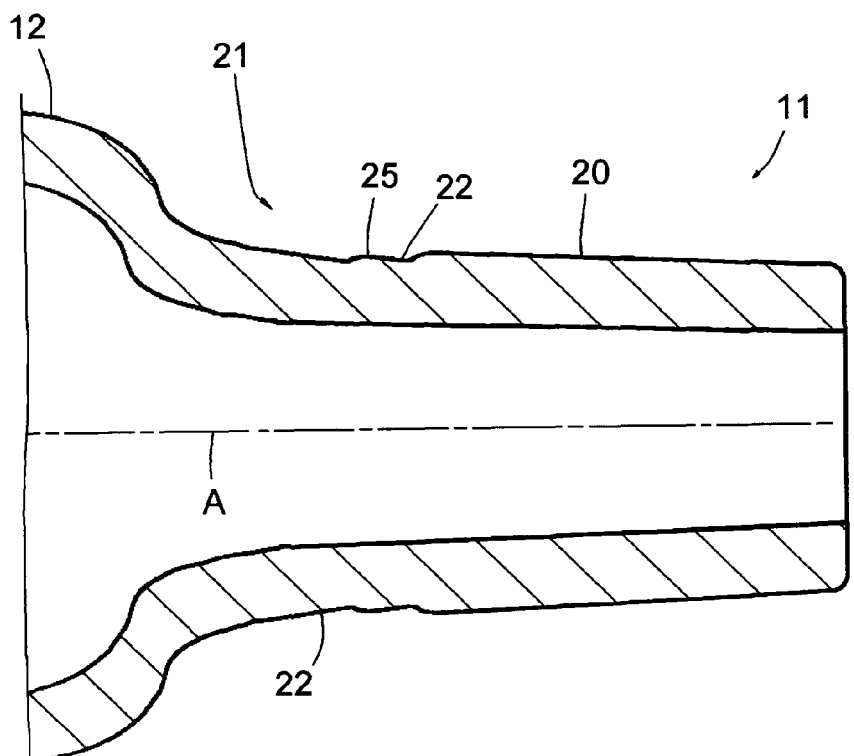
FIG. 13 is an enlarged view similar to FIG. 8 of a tip according to another embodiment.

FIG. 13 show an embodiment of a tip 11 of a syringe body made of glass, in which the mounting area 21 includes a tapered wall forming the bottom 22 and a projection 25 in the form of a rounded circumferential bump.

It appears from the foregoing that the invention provides a connection assembly having the essential advantages mentioned above.

It goes without saying that the invention is not limited to the exemplary embodiments described above but includes all the other embodiments encompassed by the appended claims.

The invention claimed is:

1. A connection assembly for a drug delivery device comprising a tip defining a longitudinal axis and including a mounting area for mounting an adaptor thereon, and said adaptor including a mounting portion of thermoplastic material, forming a radial surface, which defines a mounting opening for mounting said adaptor onto said tip, said mounting area includes at least one first portion having an outer surface which is located at a first distance from said longitudinal axis and at least one second portion, adjacent to said first portion, having an outer surface which is located at a second distance from said longitudinal axis, said second distance being different from said first distance, said radial surface being located after assembly of said adaptor over said first portion and said second portion;

said mounting opening and said at least one first portion and second portion dimensioned such that said radial surface of said mounting portion is in contact with the outer surfaces of both said first portion and said second portion;

wherein said first portion is in the form of a circumferential rib or groove centered on said longitudinal axis and said second portion is in the form of a circumferential surface centered on said longitudinal axis, adjacent said rib or groove, said first distance and second distance being the respective radiuses of said rib or groove and circumferential surface.

2. The connection assembly according to claim 1, wherein said mounting portion and at least one of said first portion and said second portion are dimensioned such that the mounting portion is compressed in a direction perpendicular to said longitudinal axis when the mounting portion is located over said first portion and said second portion.

3. The connection assembly according to claim 1, wherein at least one of said outer surface of said first portion and of said second portion exhibit a round cross-section in a plane containing said longitudinal axis.

4. The connection assembly according to claim 1, wherein at least one of said outer surface of said first portion and of said second portion contain at least one ridge in a cross-section of a plane containing said longitudinal axis.

5. The connection assembly according to claim 1, wherein at least one of said outer surface of said first portion and of said second portion contain a surface parallel to said longitudinal axis in a cross-section of a plane containing said longitudinal axis.

6. The connection assembly according to claim 1, wherein at least one of said outer surface of said first portion and of said second portion contain a surface that is not parallel to said longitudinal axis, in a cross-section of a plane containing said longitudinal axis, said first distance and said second distance being the minimum distance of said at least one of said first and second portion to said longitudinal axis.

7. The connection assembly according to claim 1, wherein at least one of said outer surface of said first portion and of said second portion comprise a cylindrical surface.

8. The connection assembly according to claim 1, wherein at least one of said outer surface of said first portion and of said second portion comprise a tapered surface.

9. The connection assembly according to claim 1, wherein the difference between said second distance and said first distance is from 0.05 to 0.20 mm.

10. The connection assembly according to claim 1, wherein said tip is the end of a syringe body allowing the connection of an injection needle to this syringe body.

11. The connection assembly according to claim 1, wherein said adaptor is a Luer type connector.

* * * * *